US00PP30022P3

(12) United States Plant Patent
Biancheri

(10) Patent No.: US PP30,022 P3
(45) Date of Patent: Dec. 25, 2018

(54) ***RANUNCULUS* PLANT NAMED 'ABATLAUA'**

(50) Latin Name: *Ranunculus asiaticus*
Varietal Denomination: ABATLAUA

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 15/731,516

(22) Filed: Jun. 20, 2017

(65) Prior Publication Data

US 2018/0020588 P1 Jan. 18, 2018

(30) Foreign Application Priority Data

Jul. 13, 2016 (QZ) ..... PBR 2016/1770

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02; A01H 5/00; A01H 6/72
See application file for complete search history.

(56) References Cited

PUBLICATIONS

Biancheri Creazioni. Fanny, retrieved on May 17, 2018, retrieved from the Internet at https://www.bianchericreazioni.it/scheda-102-fanny, one page. (Year: 2018).*

Missouri Botanical Garden for *Ranunculus asiaticus,* retrieved on May 15, 2018, retrieved from the Internet at http://www.missouribotanicalgarden.org/PlantFinder/PlantFinderDetails.aspx?kempercode=a471, 2 pp. (Year: 2018).*

New Plants and Flowers. *Ranunculus* Pon-Pon Malva runs for Glazen Tulp 2016 award 2015, retrieved on May 17, 2018, retrieved from the Internet at http://www.newplantsandflowers.com/ranunculus-pon-pon-malva-runs-for-glazen-tulp-2016-award/, 3 pp. (Year: 2015).*

* cited by examiner

*Primary Examiner* — June Hwu
(74) *Attorney, Agent, or Firm* — Cassandra Bright

(57) ABSTRACT

A new and distinct *Ranunculus* cultivar named 'ABATLAUA' is disclosed, characterized by a unique combination of colors in the corolla, including greens and purples. The corolla has a rounded shape when it is fully open. The petals are uniquely rippled in texture. Plants are highly productive and flowers have an exceptionally long vase life. The new variety is a *Ranunculus*, normally produced as a cut flower and potentially useful as an ornamental plant.

2 Drawing Sheets

Latin name of the genus and species: *Ranunculus asiaticus*.

Variety denomination: 'ABATLAUA'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2007.

The seed parent is the, unpatented, proprietary variety referred to as *Ranunculus* 'PPBsfRS159.05'. The pollen parent is the unpatented, proprietary variety referred to as *Ranunculus* 'AB5'. The new variety was discovered in 2010 by the inventor in a group of seedlings resulting from the 2007 crossing, in a research greenhouse in Camporosso Mare, Italy.

Asexual reproduction of the new cultivar was first performed by vegetative division of buds sprouting from the tuberous root of the selected plant. Subsequent propagation has been performed by tissue culture. First propagation took place at a research greenhouse in Camporosso Mare, Italy in 2010 and has shown that the unique features of this cultivar are stable and reproduced true to type in multiple successive generations.

SUMMARY OF THE INVENTION

The cultivar 'ABATLAUA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABATLAUA' These characteristics in combination distinguish 'ABATLAUA' as a new and distinct *Ranunculus* cultivar:

1. Unique combination of green and purple colors in the corolla.
2. Rounded shape of the corolla when it is fully open.
3. Petals have a unique rippled texture.
4. Exceptionally long vase life.
5. High productivity.

PARENT COMPARISON

Plants of the new cultivar 'ABATLAUA' are similar to plants of the seed parent, in most horticultural characteristics, however, plants of the new cultivar 'ABATLAUA' differ in the following;

1. Flower color of the new variety is different.

Plants of the new cultivar 'ABATLAUA' are similar to plants of the pollen parent, in most horticultural characteristics, however, plants of the new cultivar 'ABATLAUA' differ in the following;

1. The pollen parent has a solid flower color.
2. Flower shape of the new variety is different.
3. Combination of colors in the corolla.

COMMERCIAL COMPARISON

Plants of the new cultivar 'ABATLAUA' are comparable to the commercial variety *Ranunculus* 'ABOSHOSSI', U.S. Plant patent application Ser. No. 15/731,515, filed concurrently. The two *Ranunculus* varieties are similar in most horticultural characteristics; however, the new variety 'ABATLAUA' differs in the following:

1. Combination of colors in the corolla; 'ABATLAUA' has a corolla which is shades of purple and green, corolla color of 'ABOSHOSSI' is shades of red and green.

BRIEF DESCRIPTION OF THE PHOTOGRAPHS

Figure 1:
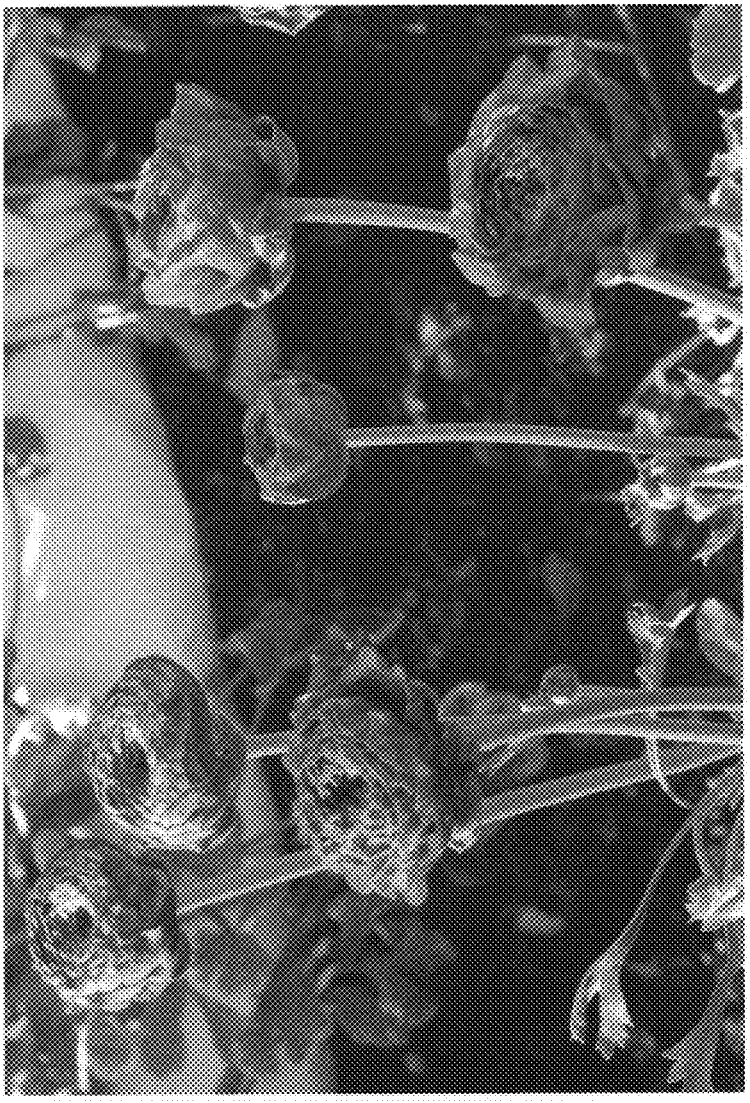

The accompanying photograph in FIG. 1 illustrates in full color flowering plants of the new variety at approximately five months old, grown in a greenhouse.

Figure 2:
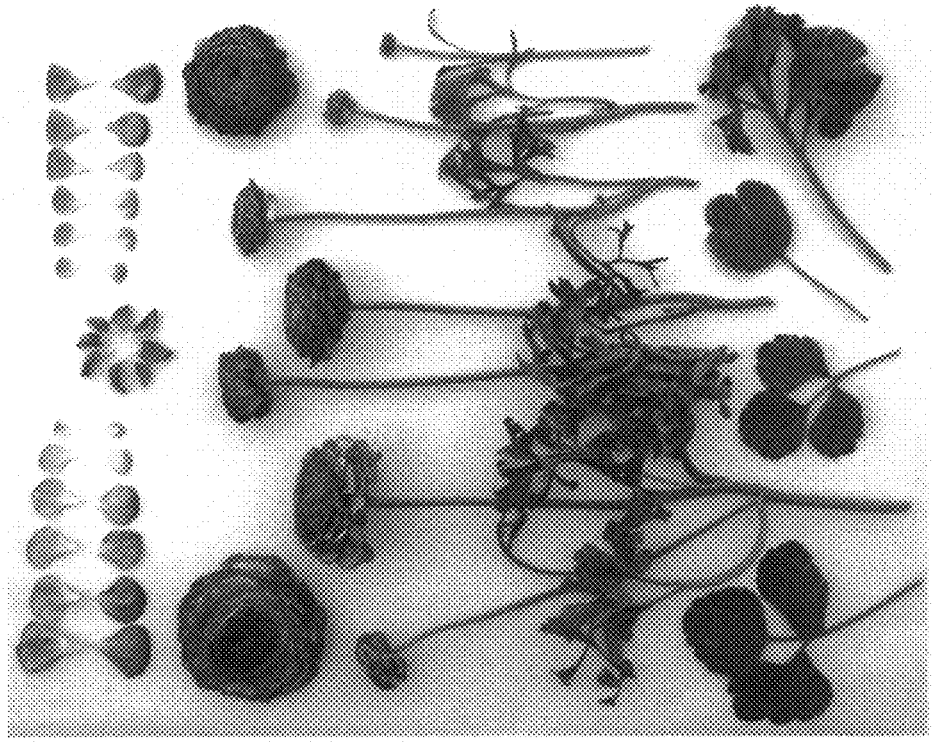

FIG. 2 illustrates a close up of plant parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 'ABATLAUA' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'ABATLAUA'.

Propagation:

*Time to rooting.*—15 days at approximately 10-12° C.

*Time to produce a rooted plantlet.*—20 days.

*Root description.*—Tuberous roots. Quantity of tubers varies significantly with age and environmental conditions. Colored tan to white, not accurately measured with R.H.S. chart.

Plant:

*Growth habit.*—Herbaceous perennial, robust plant, semi-erect vegetation.

*Height to top flower.*—45 to 50 cm.

*Plant spread.*—50 to 70 cm.

*Growth rate.*—Medium.

*Branching characteristics.*—Main floral stems grow from a basal rosette, with 1 or 2 lateral branches, each one of which has a flower.

*Length of lateral branches.*—40 to 50 cm.

*Diameter of lateral branches.*—0.5 to 0.7 cm.

*Texture of lateral branches.*—Slightly tomentose.

*Internode length.*—Internodes are extremely close together, forming a basal rosette.

*Strength of lateral branches.*—Medium.

*Color of lateral branches.*—Yellow Green (RHS 146C).

*Aspect/angle of branches.*—20° to 25°.

*Number of leaves per lateral branch.*—Usually 2.

Foliage:

*Leaf.*—The leaves, usually numerous, have a marked heterophyllia (significant variation in leaf shape, size and arrangement on a same plant), Simple, biternate and ternate leaves appear on the same plant, in relation to the degree of development (young leaf and mature leaf) and their position on the plant (basal leaf — leaf at the base of the plant — and cauline leaf — leaf inserted at the nodes of the floral stem).

*Leaf at the base of the plant.*—Arrangement: Simple (young leaf, YL); Biternate (mature leaf, ML). Average Length: 10 to 25 cm. Average Width: 10 to 20 cm. Overall Shape of blade: Obovate (young leaf); Palmatipartite (mature leaf). Dissected leaves, describe lobes, quantity of dissection: Young leaves are generally not lobed; mature leaves are generally divided in 3 parts, each one of which is further divided in 3 or more lobes. Apex: Rounded (young leaf); Acute (mature leaf). Base: Rounded. Attachment: Base of the plant. Margin: Crenate (young leaf); Dentate (mature leaf). Texture of top surface: Slightly tomentose. Texture of bottom surface: Slightly tomentose. Appearance of top surface: Glossy. Appearance bottom surface: Glossy. Leaf internode length: The internodes are extremely close together, forming a basal rosette. Color: Young foliage upper side: Green (RHS 138A). Young foliage under side: Green (RHS 138B). Mature foliage upper side: Green (RHS 137B). Mature foliage under side: Green (RHS 138B). Venation: Type: Dichotomous; plunging in to the limb at the upper surface; raised on the limb at the lower surface. Venation color upper side: Yellow Green (RHS 146C). Venation color under side: Yellow Green (RHS 146C). Petiole: Petiole: Long, tubular, rigid. Length: 12 to 18 cm. Diameter: 0.2 to 0.7 cm. Pubescence: Slightly tomentose. Color: Yellow Green (RHS 146C).

*Leaf inserted at the nodes of the floral stems (SL).*—Arrangement: Biternate. Average Length: 15 to 20 cm. Average Width: 10 to 15 cm. Overall Shape of blade: Palmatipartite. Dissected leaves, describe lobes, quantity of dissection: Generally divided in 3 parts, each one of which is further divided in many deeply incised lobes. Apex: Acute. Base: Acute. Attachment: Floral stems. Margin: Dentate. Texture of top surface: Slightly tomentose. Texture of bottom surface: Slightly tomentose. Appearance of top surface: Matte. Appearance bottom surface: Glossy. Leaf internode length: 3 to 4 cm. Color: foliage upper side: Green (RHS 137B). foliage under side: Green (RHS 138B). Venation: Type: Dichotomous, plunging in to the limb at the upper surface and raised on the limb at the lower surface. Venation color upper side: Yellow Green (RHS 146C). Venation color under side: Yellow Green (RHS 146C). Petiole: Petiole: Long, slightly flat, rigid. Length: 8 to 16 cm. Diameter: 0.3 to 0.5 cm. Pubescence: Slightly tomentose. Color: YellowGreen (RHS 146C).

Flower:

*Bloom period.*—Winter to Spring.

*Vase life* (*cut flower*).—15 to 20 days.

*Persistent or self-cleaning.*—Self-Cleaning.

*Number of flowers per plant.*—9-12.

*Bud.*—Closed bud (CB): Shape: Flattened globular. Length: 0.5 to 1.0 cm. Diameter: 0.7 to 1.5 cm. Color: Green (RHS 137B) at the center; Purple (RHS N79B) along the venations and Yellow Green (RHS 145B) near the base. Slightly open bud (OB): Shape: Flattened globular. Length: 0.7 to 1.0 cm. Diameter: 1.6 to 2.0 cm. Color: Yellow Green (RHS 146C); Purple (RHS N79B/N79C) near the margins.

*Flower size* ($OF_{1.2}$).—Diameter: 8 to 15 cm. Height: 2.5 to 3.5 cm.

*Corolla* ($OF_{1.2}$).—Round, regular, in the form of a flattened sphere with slightly festooned edges. Petals: Arrangement: Imbricated, disposed on the receptacle in very tight verticils. The size of the petals is quite variable, according to the position in the corolla, decreasing from the exterior toward the center. The average size of fully developed petal is as follows: Length: 4.0 to 5.5 cm. Width: 3.5 to 5.0 cm. Quantity: Double flower, petals are very numerous approximately 120 to 180. Texture: Silky, thin, resistant. Apex: Rounded. Shape: Obovate. Margin: Entire or slightly Crenate to Sinuate. Aspect: Rhomboid, concave with moderately reflexed apex when flower is fully opened. Color when opening (CF): Upper surface: Purple (RHS N79C) near the margin; Yellow Green (RHS 146C) from the center towards base. Lower surface: Purple (RHS N79C) near the margin; sub-marginal coloration near Red Purple (RHS 71A) and towards base Yellow Green (RHS 146C). Color Fully opened ($OF_1$): Upper surface ($PU_1$): Purple (RHS N79C) near the margin; Sub-marginal coloration near Red-Purple 71A until nearly center, center to base Yellow-Green 146C, base White 155D. Lower surface ($PL_1$): Purple (RHS N79C) near the margin Sub-marginal coloration near Red-Purple 71A until nearly center, center to base Yellow-Green 146C, base White 155D. Other cultural improvements or features: In this variety, the colors of the corolla could present a lack of Purple tones and an increase of Green tones. This is already noticeable in the flowers that are opening and is present in those that are wide open ($OF_2$; $PU_2$. $PL_2$). This variation of color, partially typical of this variety, is accentuated in particular growing conditions, in relation to light exposure, to the temperature and to the different composition of fertilizers used by the various farms. Calyx to Sepals (S): Quantity per flower: 6 to 8. Shape: Concave, moderately incurved. Length: 2.5 to 3.5 cm. Width: 0.8 to 1.8 cm. Apex: Acute to Suboptuse. Base: Flat to Slightly rounded. Margin: Entire; Dentate at the apex. Texture: Lower surface is tomentose; Upper surface is glabrous. Color Upper Surface: Green (RHS 138B). Color Lower Surface: Green (RHS 137B); Red Purple (RHS 71A) along venation.

*Peduncle.*—None.

*Pedicel.*—Length: 35 to 45 cm. Diameter: 0.8 to 1.2 cm. Color: Yellow Green (RHS 146C). Orientation: Upright, straight, rigid. Pubescence: Slightly tomentose.

*Fragrance.*—None.

Reproductive organs:

*Androecium.*—Stamens: Transformed as petals.

*Gynoecium.*—The pistils are numerous, short, fused together at the center of the corolla in a Strong Yellow Green (RHS 144B) and Purple (RHS N79B), irregular, dome-shaped apocarpous gynoecium.

*Nectar gland.*—Absent.

Other characteristics:

*Seeds and fruits.*—Seeds and fruit production not observed.

*Disease to pest resistance.*—Neither resistance nor susceptibility to normal diseases and pests of *Ranunculus* has been observed.

*Temperature tolerance.*—Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABATLAUA' as herein illustrated and described.

* * * * *